(12) United States Patent
Ji et al.

(10) Patent No.: US 8,647,278 B2
(45) Date of Patent: Feb. 11, 2014

(54) METHOD AND SYSTEM FOR NON-INVASIVE INTRACRANIAL PRESSURE MONITORING

(75) Inventors: Zhong Ji, Shapingba (CN); Li Yang, Shapingba (CN); Shuang Yang, San Diego, CA (US); Mingxi Zhao, Shapingba (CN)

(73) Assignee: Chongqing University, Shapingba, Chongqing (CN)

( * ) Notice: Subject to any disclaimer, the term of this patent is extended or adjusted under 35 U.S.C. 154(b) by 0 days.

(21) Appl. No.: 13/280,778

(22) Filed: Oct. 25, 2011

(65) Prior Publication Data

US 2012/0101387 A1    Apr. 26, 2012

Related U.S. Application Data

(60) Provisional application No. 61/407,012, filed on Oct. 26, 2010.

(51) Int. Cl.
*A61B 8/00* (2006.01)
(52) U.S. Cl.
USPC ............................ 600/454; 600/438; 600/437
(58) Field of Classification Search
USPC ................................................ 600/437–469
See application file for complete search history.

(56) References Cited

U.S. PATENT DOCUMENTS

| 7,877,146 | B2* | 1/2011 | Rezai et al. | 607/42 |
| 8,109,880 | B1* | 2/2012 | Pranevicius et al. | 600/490 |
| 8,394,025 | B2* | 3/2013 | Ragauskas et al. | 600/438 |
| 2006/0206037 | A1* | 9/2006 | Braxton | 600/561 |
| 2009/0287084 | A1* | 11/2009 | Ragauskas et al. | 600/454 |
| 2010/0331684 | A1* | 12/2010 | Ragauskas et al. | 600/438 |
| 2011/0152974 | A1* | 6/2011 | Rezai et al. | 607/62 |
| 2012/0238885 | A1* | 9/2012 | Ragauskas et al. | 600/483 |

* cited by examiner

*Primary Examiner* — Sanjay Cattungal
(74) *Attorney, Agent, or Firm* — Mateo Aboy; Aboy & Associates PC

(57) ABSTRACT

Disclosed embodiments include a system and a method for determining intracranial pressure (ICP) of a subject that comprises: (a) applying transcranial Doppler (TCD) to determine the middle cerebral artery (MCA) velocity of the subject and estimating changes in the ICP continuously based on a functional mapping that relates arterial blood pressure (ABP) and cerebral blood flow velocity (CBFV) to ICP, resulting in an estimated ICP trend; (b) generating a flash visual evoked potential (FVEP) on the subject, processing a detected FVEP signal and obtaining an estimated ICP; and (c) combining the estimated ICP trend from TCD CBFV and ABP with the estimated ICP obtained by signal processing of the detected FVEP signal to periodically correct the trend and obtain a non-invasive measure of ICP.

13 Claims, 6 Drawing Sheets

METHOD AND SYSTEM FOR NON-INVASIVE INTRACRANIAL PRESSURE MONITORING

CROSS-REFERENCE TO RELATED APPLICATIONS

This application claims the benefit of U.S. Provisional Application No. 61/407,012 filed on 2010-10-26 by the present inventors, which is incorporated herein by reference.

TECHNICAL FIELD

Disclosed embodiments relate to methods and systems for monitoring of intracranial pressure. Specifically, they relate to methods and systems for non-invasive monitoring of intracranial pressure.

BACKGROUND

Intracranial pressure (ICP) is closely related to cerebral perfusion (blood flow in the brain). Elevated ICP reduces cerebral perfusion pressure, and if uncontrolled, results in vomiting, headaches, blurred vision, or loss of consciousness, escalating to permanent brain damage. Increased ICP is a medical/surgical emergency, and in severe cases, disability and death may occur.

Although several non-invasive techniques of measuring ICP have been proposed during the last decade, typically ICP monitoring is achieved by using sensors implanted within the cranium, or external sensors connected to the measurement site in the cranium with a fluid-filled catheter. These approaches are invasive, generating risk of intracranial infection and pain for the patient, and require neurosurgical expertise for their implantation. Moreover, long term monitoring of ICP often requires significant restriction on the movement of a patient. The most common invasive procedure is the lumbar puncture where a catheter with a pressure-sensing device is placed in the lumbar subarachnoid space.

Non-invasive assessment of ICP has been pursued with several approaches that are based on different physical principles. These approaches share the common idea of measuring an alternative physical variable that relates to the change of ICP. The accepted and commercially available technique for non-invasive estimation and monitoring of ICP consists of taking a computed tomography (CT) or other image of the head, interpreting the image and observing changes in various features. This method requires a high level of skill to read and assess the images and requires that the patient be brought to the imaging equipment. In many cases, a scan is delayed or put off simply because the patient is not stable enough to be moved. Even after the patient is stable, the various tubes and equipment connections to the patient have to be accounted for during the trip to the CT area, and additional personnel are often required, with a respective increase in cost. In addition, the scans themselves are single measurements, of which at least two are required to assess subtle-changes and variations. A series of scans could approximate continuous monitoring, but this is not practical.

Other non-invasive ICP monitoring techniques have been developed. A non-invasive ICP monitoring system is taught in U.S. Pat. No. 4,841,986. This system is based on fine volume measurements of the external auditory canal during elicitation of the human stapedial reflex. U.S. Pat. No. 5,919,144 discloses a non-invasive system based on real-time analysis of acoustic interaction with the brain and changes in tissue acoustic properties as ICP changes. Electromagnetic techniques are disclosed in U.S. Pat. No. 4,690,149. Ultrasonic or vibratory techniques are disclosed in U.S. Pat. No. 3,872,858. Jugular vein occlusion techniques are disclosed in U.S. Pat. No. 4,204,547. Another technique stated to be non-invasive utilizes a nuclear powered pressure sensor designed to be implanted totally under the scalp of the patient and is disclosed in U.S. Pat. No. 4,141,348. A method for determining ICP based on acoustic data from a target site is disclosed in U.S. Pat. No. 7,547,283.

Each of the currently used or medically accepted methods for ICP assessment is deficient in some way. Because of the deficits in current ICP measurement methodologies, there is a need for an easily administered non-invasive (or minimally invasive) method for continuous long-term monitoring of ICP.

BRIEF DESCRIPTION OF THE DRAWINGS OF EMBODIMENTS

Disclosed embodiments are illustrated by way of example, and not by way of limitation, in the figures of the accompanying drawings.

DESCRIPTION OF EMBODIMENTS

Figure 1:
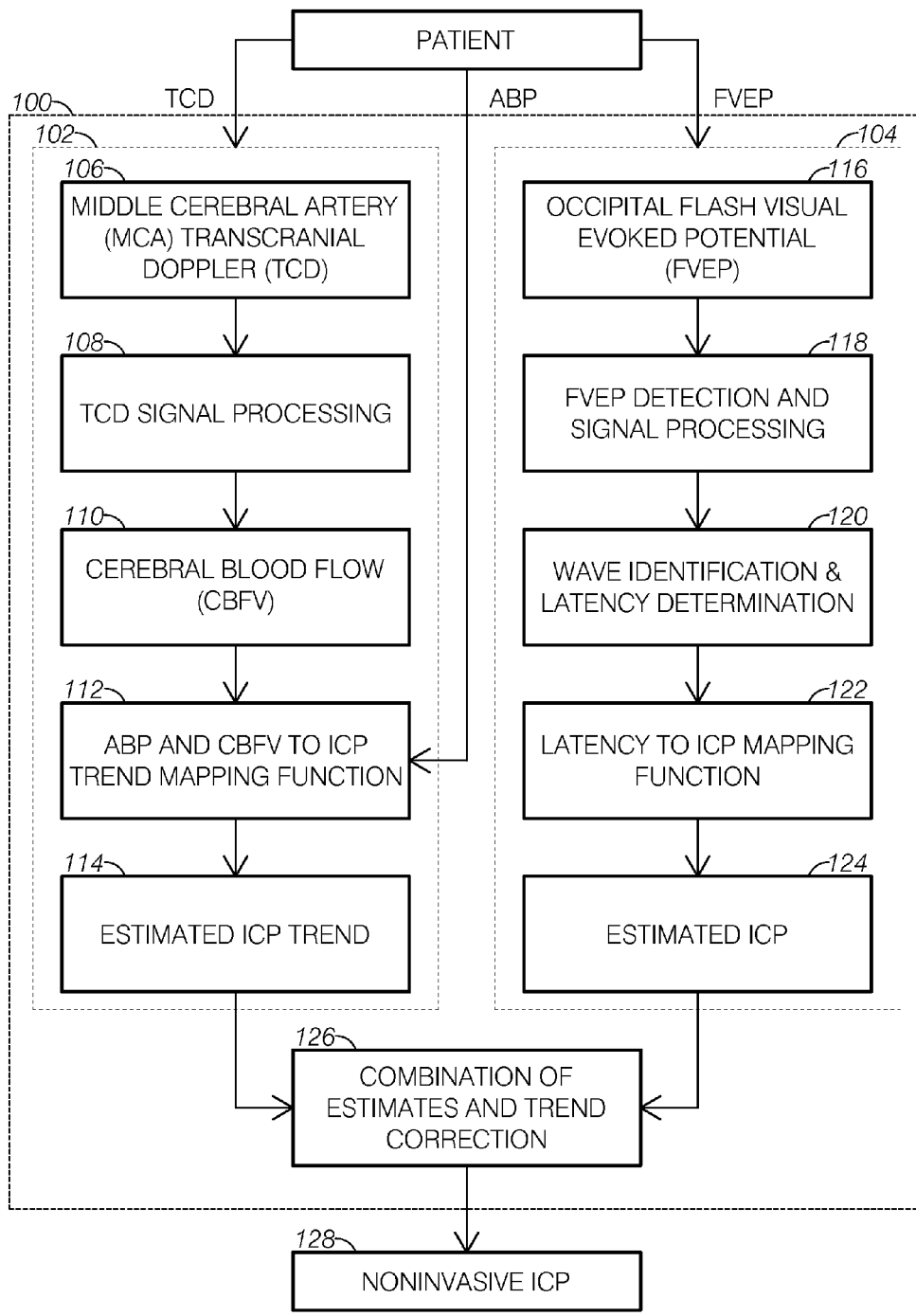
FIG. 1 shows a block diagram according to one embodiment of the system and method.

Disclosed embodiments are directed to a method, apparatus, and system for determining intracranial pressure (ICP) of a subject. The method, apparatus, and system transform non-invasive physiologic signals to determine ICP noninvasively. According to one embodiment, as shown in FIG. 1, the method for ICP determination 100 is comprised of (a) acquiring, processing, and analyzing transcranial Doppler (TCD) signals 102 and (b) acquiring, processing, and analyzing flash visual evoked potential (FVEP) signals 104. Each method/subsystem (e.g., 102 and 104) produces a noninvasive estimate of ICP signal characteristics, and these estimates are combined 126 to generate a final estimate of noninvasive ICP 128.

According to one embodiment, the method comprises: (a) applying transcranial Doppler (TCD) to determine the middle cerebral artery (MCA) 106 velocity of the subject, processing it 108, obtaining CBFV 110, and estimating changes in the ICP continuously based on a functional mapping that relates arterial blood pressure (ABP) and cerebral blood flow velocity (CBFV) to ICP 112, resulting in an estimated ICP trend 114; (b) generating a flash visual evoked potential (FVEP) on the subject 116, processing a detected FVEP signal 118, performing wave identification and latency and obtaining an estimated ICP 124; and (c) combining 126 the estimated ICP trend from TCD CBFV and ABP 114 with the estimated ICP obtained by signal processing of the detected FVEP signal 124 to periodically correct the trend and obtain a non-invasive measure of ICP 128. In a particular embodiment, the method step of obtaining an estimated ICP comprises: (a) applying a flash stimulation to the eyes of the subject resulting in a generated FVEP signal in the visual pathway of the subject; (b) detecting the generated FVEP signal by electrodes placed on the occipital area; (c) performing signal processing 118 to amplify, filter, detect features, and measure a latency 120 of a feature on the FVEP signal correlated with ICP; and (d) estimating ICP based on a functional mapping that relates the latency on the FVEP signal and ICP 112. More particularly, and without limitation, the latency of a feature 120 on the FVEP signal is obtained by measuring a latency change on the FVEP signal second negative wave (N2) wave. According to one specific embodiment, the method step of performing signal processing comprises (a) amplifying; (b) filtering; and (c) denoising the FVEP signal using independent component analysis (ICA) based on a FastICA method, synchronous averaging, and wavelet decomposition (alternative embodiments employ other signal processing techniques including optimal filtering, nonlinear filtering, Kalman filtering, extended Kalman filtering, participle filtering, complexity techniques, and spectral analysis techniques). It can also further include identifying the N2 wave and deriving ICP values corresponding to the two visual pathways, and identifying the N2 wave may performed automatically using digital signal processing (DSP) or semi-automatically depending on the condition of the FVEP signal. In a particular implementation, and without limitation, the application of flash visual evoked potential comprises: a) applying a plurality of disc-like electrodes or Ag/AgCl needle electrodes to the occipital lobes of the subject, the electrodes are electrically connected to a signal processing device; b) applying a pulsed flash of light to both eyes of the subject using a flash stimulation device, the pulsed flash has a pre-determined pulse frequency; c) capturing the resulting flash visual evoked potential signals generated in the left and right visual pathways to the occipital lobes of the subject by the signal processing device via the electrodes; d) performing signal processing on the flash visual evoked potential signals using the signal processing device, the signal processing includes at least one high gain amplifier and an analog-to-digital converter, digital signal processing, and outputting enhanced flash visual evoked potential signals to a computing device; e) determining the latency value of the N2 wave of the flash visual evoked potential; and f) applying a predetermined linear relationship between latency of the second negative wave and invasive intracranial pressure to derive the intracranial pressure of the subject. In particular embodiments, the electrodes may be solely disc-like electrodes, whereby intracranial pressure of the subject can be determined entirely non-invasively. In one embodiment, the pre-determined frequency of the pulsed flash is adjustable. More particularly, and without limitation, in one embodiment the plurality of disc-like electrodes or Ag/AgCl needle electrodes consist of four electrodes, two of the four electrodes are sampling electrodes placed on the occipital lobes of the subject, one of the four electrodes is a reference electrode placed on the hair line of the forehead of the subject, and one of the four electrodes is a ground electrode placed on the glabellum of the subject. Additionally, in a particular embodiment the representation of the enhanced flash visual evoked potential signals on the computing device further includes the option of displaying one of a group consisting of a representation of an enhanced flash visual evoked potential signal for the left visual pathway to the occipital lobes of the subject, a representation of an enhanced flash visual evoked potential signal for the right visual pathway to the occipital lobes of the subject, a representation of superimposed enhanced flash visual evoked potential signals for the left and right visual pathways to the occipital lobes of the subject, and a representation of any stored enhanced flash visual evoked potential signal or combination of enhanced flash visual evoked potential signals.

According to another particular disclosed embodiment, and without limitation, the method for monitoring the intracranial pressure of a subject by contemporaneous application of flash visual evoked potential and transcranial Doppler, comprising: (a) periodically applying flash visual evoked potential to the subject to determine the latency value of the second negative wave, and applying the linear relationship between latency of the second negative wave and invasive intracranial pressure to periodically derive the absolute intracranial pressure of the subject; (b) continuously applying transcranial Doppler to monitor arterial blood pressure and blood flow velocity in the middle cerebral artery of the subject, and applying a nonlinear mapping function to derive the intracranial pressure change trend based on the hemodynamic properties of the arterial blood pressure and the blood flow velocity readings; and (c) using the periodically derived absolute intracranial pressure values to correct the intracranial pressure change trend; whereby the intracranial pressure of the subject can be continuously monitored with high precision. In one embodiment, and without limitation, the mapping function from N2 latency to ICP is given by $$y(t)=at^2+c \quad (1)$$

where y(t) denotes the noninvasive ICP estimated, t is the latency of the N2 wave in the FVEP signal, a is an empirically determined adjustment factor, and c is a bias correcting term. The resulting estimated y(t) is linearly correlated with invasive ICP values. Alternative embodiments are possible, including any function from t to y(t) whose parameters can be calculated empirically (e.g., least squares, regularization techniques, regression techniques, nonlinear functions, neural networks, etc).

According to one particular embodiment, and without limitation, the method involves: 1) sampling the FVEP signal, TCD ultrasonic signals, and ABP signals to the computer (or medical device) before using the intracranial pressure noninvasive detection device (the actual object dynamic waveform of training samples is also sampled to the computer synchronously by using the invasive intracranial pressure monitor connected to the computer); 2) choosing the patients with different intracranial pressure related diseases as the training sample objects, and obtain the FVEP signal, TCD ultrasound signals, and intracranial pressure dynamic variation waveform of these training samples by using the computer; 3) applying the functional mapping relationship between the various detected parameters and intracranial pressure by analyzing the sampled FVEP signal, TCD ultrasound signal, ABP signal (the corresponding weight values can be determined according to the effects of the different parameters to intracranial pressure change, and the ICP evaluation function model can be built by summing the mapping function relationship between the changes of different parameters and ICP based on the weight values). In this embodiment the ICP evaluation function model is $$V(t) = \sum_{i=1}^{N} \alpha_i f(x_i(t)) \quad (2)$$

where V(t) denotes the measured values of the ICP dynamic waveform as a function of time t, N denotes the number of signal parameters, $x_i(t)$ denotes the ith parameter as function of time, $f(x_i(t))$ denotes the mapping relationship between the changes of the parameters and ICP, and $\alpha_i$ represents the corresponding weight value of the ith parameter $\Sigma i=1^N {}_{\alpha_i}=1$. Additionally, in one embodiment, the information database and individual compensation function of the samples are stored in the computer. The information database is used to store the sample information. The individual compensation function is used to record the mapping relationship between ICP testing compensation and individual information. The individual information is used as the input for the individual compensation function, and to determine the intracranial pressure testing compensation value after obtaining the intracranial dynamic variation waveform by ICP evaluation function model. The corrected ICP dynamic change waveform can be obtained by using the ICP compensation value to compensate and correct the ICP testing values of the dynamic change waveform. The ICP corrected evaluation function model of the proposed method can be described as:

$$V_C(t) = \sum_{i=1}^{N} \alpha_i f(x_i(t)) + \Delta_s(Y) \qquad (3)$$

where $V_C(t)$ denotes the corrected ICP values of dynamic changes waveform, and $\Delta_s(Y)$ denotes the ICP compensation value with individual information.

According to one particular embodiment of the method for determining the ICP trend of a subject, TCD is applied to the middle cerebral artery of the subject in order to obtain readings for cerebral blood flow velocity (CBFV) to be combined with arterial blood pressure (ABP). Hemodynamic parameters related to the change of ICP can be extracted from the ABP and CBFV readings, and by using an empirically estimated mapping function, these parameters can be correlated to the change of ICP of the subject. In this way, through the continuous application of TCD, ICP trend measurements for the subject can be obtained.

Embodiments of the aforementioned method use a database management system to extract the hemodynamic parameters related to the change of ICP from ABP and CBFV readings, and to apply the nonlinear mapping function to track the ICP trend of the subject.

Figure 4:
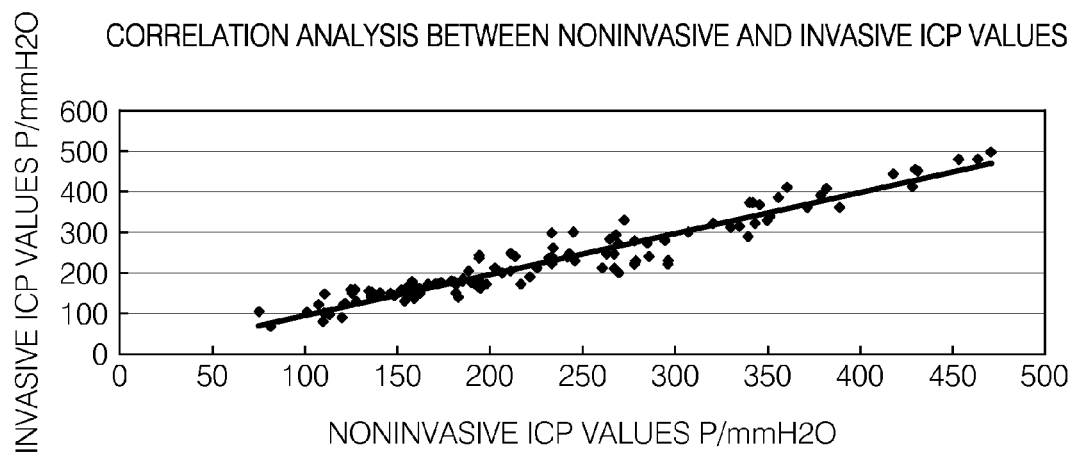
FIG. 4 illustrates a graph representing a correlation analysis between non-invasive and invasive ICP values.

According to one particular embodiment of the method for determining the ICP of a subject, a pulsed flash of light is applied to the eyes of the subject, thereby generating FVEP in the visual pathways to the occipital lobes of the subject. The FVEP signals are detected by disc-like electrodes. The weak FVEP signals are amplified, converted to digital values using an A/D converter, and an enhanced FVEP signal is extracted using advanced signal processing techniques. The enhanced FVEP signal is then transmitted to a computer for storage and waveform display. The latency of the intracranial second negative (N2) wave in the enhanced FVEP signal is determined. By applying a mathematical relationship between latency of the N2 wave in the FVEP signal and invasive intracranial pressure, as shown in FIG. 4, an absolute ICP value is obtained non-invasively and quantitatively. In this way, through the periodic application of FVEP to the subject, periodic ICP measurements for the subject can be obtained.

Alternative embodiments of the aforementioned method monitor FVEP generated in the visual pathways to the occipital lobes of a subject through use of Ag/AgCl needles instead of disc-like electrodes. Ag/AgCl needles are usually required for cerebral trauma patients with head bandages that preclude the use of disc-like electrodes. Nevertheless the use of Ag/AgCl needles is only minimally invasive.

Alternative embodiments of a method for non-invasive ICP monitoring, apply FVEP every 5, 10 or 30 minutes in order to generate absolute ICP measurements for the purpose of periodic correction to the TCD trend values for ICP. The interval between each application of FVEP is based on TCD measurements.

Figure 3:
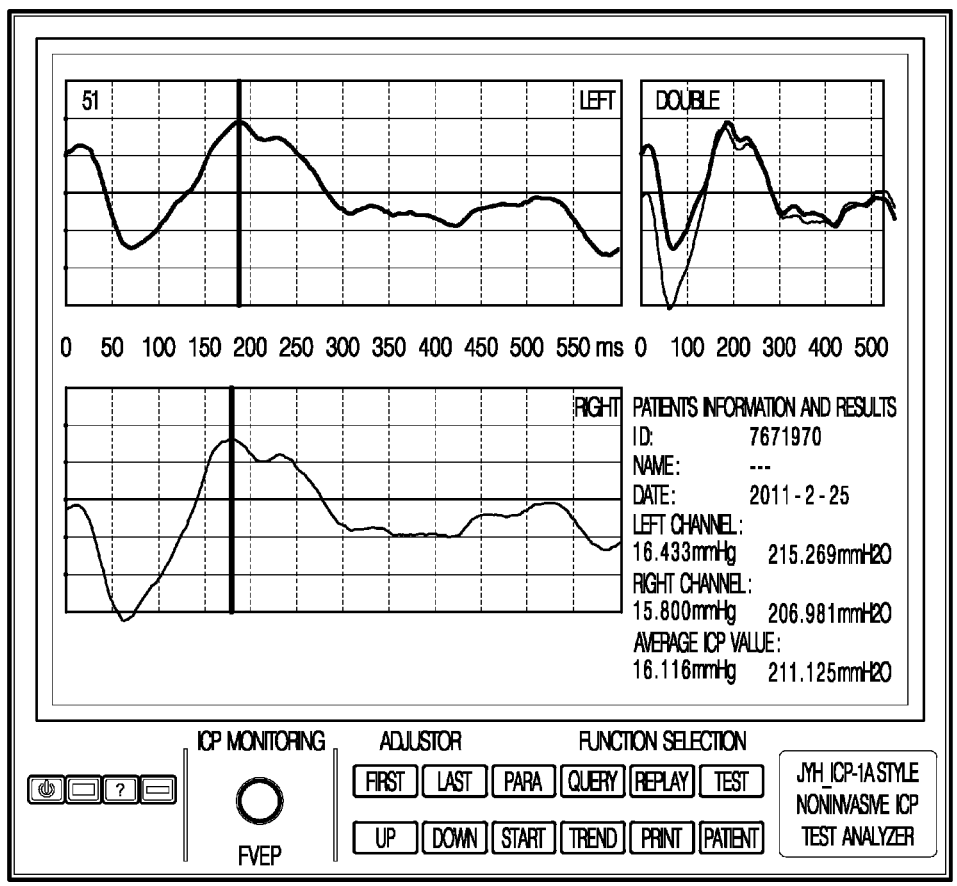
FIG. 3 illustrates an image representing one embodiment of the system graphical user interface for display and analysis of flash visual evoked potential (FVEP) waveforms by a computing device.

According to one particular embodiment of a software graphical user interface for display and analysis of FVEP waveforms by a computing device, shown in FIG. 3, the lower half of the graphical user interface is composed of functional buttons, which facilitate recall, analysis, display and management functions of subject data and FVEP signal waveforms. The upper left-hand window of the graphical user interface displays the FVEP signal waveforms for the left and right pathways to the occipital lobes. The abscissa (x-axis) is the latency of waveform and is used to determine the latency of the N2 wave. The ordinate values (y-axis) are not important because only the latency of the N2 wave is required in order to derive ICP values. The location of the N2 wave can be determined automatically by software based on the condition of the FVEP signal. Usually the N2 wave has the largest amplitude value, however if this is not the case, the decision logic are used to decide the location of the N2 wave. The right window displays information about a subject including ID, name of a subject, date of measurement, ICP values for left and right visual pathways, and the mean ICP value. Alternative display options for the upper left-hand window of the graphical user interface include display of super-imposed FVEP signal waveforms.

According to one particular embodiment of the correlation analysis between non-invasive and invasive ICP values based on the empirical results of clinical experiments, shown in FIG. 4. In this particular study used to determine the degree of correlation between the gold-standard invasive ICP and the estimated (noninvasive) ICP generated by the proposed method/system, there are 134 clinical subjects including 80 males and 54 females. The youngest participant was 12, the oldest was 81, and the mean age was 42. The clinical diagnosis included 48 patients with cerebral hemorrhage, 41 patients with cerebral trauma, 16 patients with hydrocephalus, 6 patients with meningitis, 3 patients with hypertensive encephalopathy, 9 patients after surgical operation of brain stem tumor, and 11 patients after surgical operation of cerebellar tumor. As shown in the correlation analysis, there is a high linear correlation between invasive ICP and the output of the proposed method (non-invasive ICP).

Figure 5:
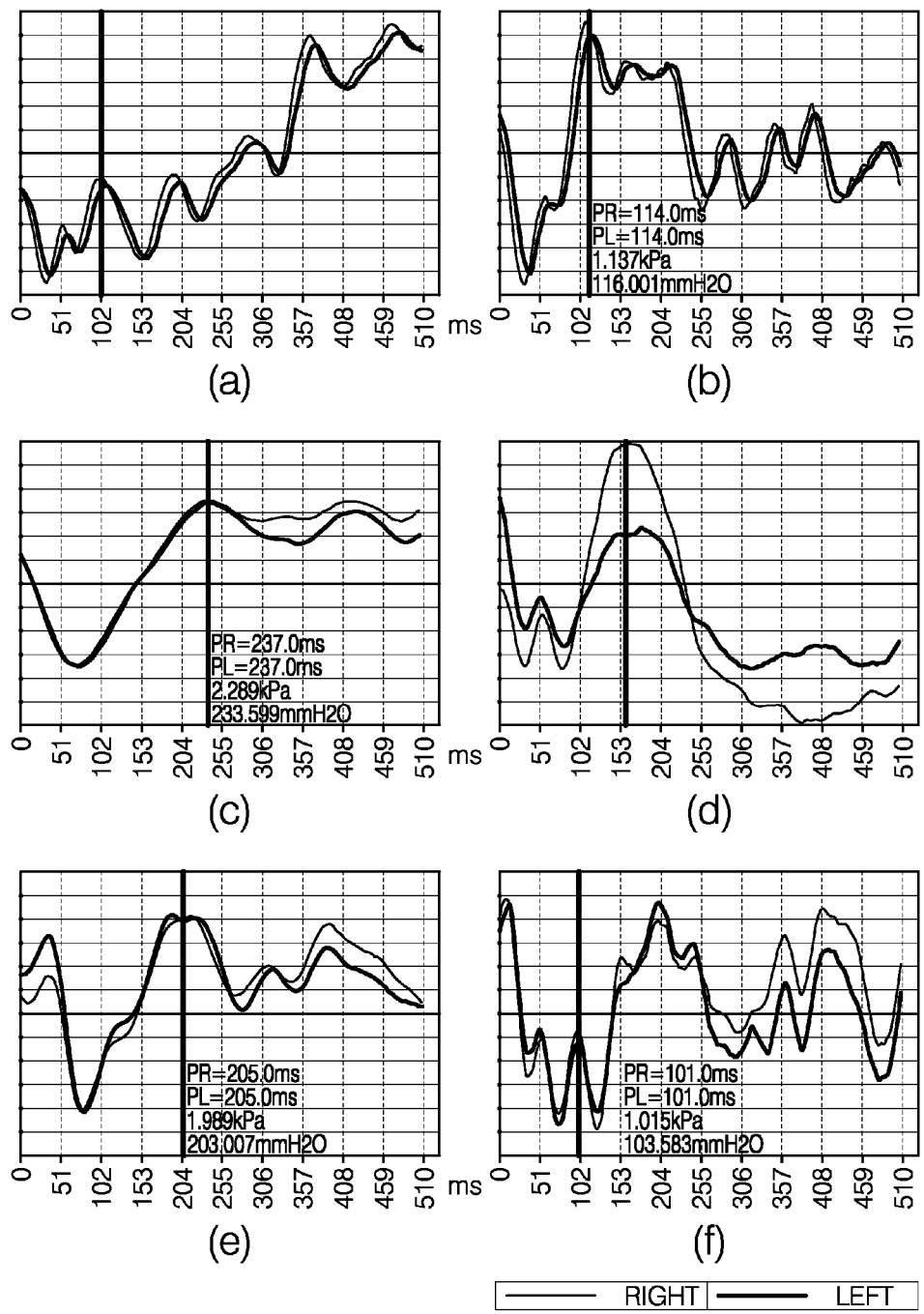
FIGS. 5A-5F illustrate images representing six examples of superimposed FVEP signal waveforms, and decision rules for identification of the N2 wave position in each example.

Examples of superimposed signal waveforms for FVEP in left and right visual pathways to the occipital lobes of a subject, and decision rules for identification of the N2 wave position, are shown in FIGS. 5A-5D. The latency of the N2 wave is defined as the position on the x-axis of the peak of the N2 wave crest. The first negative (N1) wave precedes the N2 wave. The decision rules are useful for identifying the N2 wave automatically by software, or semi-automatically in the case where automatic determination fails. Automatic identification of the N2 wave is accomplished using DSP. However, in some cases, it may be difficult to show the N2 wave position exactly by the automatic identification method, in which case a doctor may be required to correct the N2 wave position, which is regarded as semi-auto detection. FIG. 5A shows the FVEP signal of a normal subject with a well-defined waveform in which the N2 wave is the second negative wave, with obvious trough and wave crest, from the left. FIG. 5B shows a less well-defined FVEP waveform in which the N1 to N2 wave transition is not so obvious. FIG. 5C shows another FVEP waveform in which the N1 to N2 wave transition does not appear. In the case of FIG. 5C, a decision rule identifies the N2 wave as the first large negative wave (with a well-defined V-type trough) in the case where an N1 wave is not completed before 90 ms. In practice, the N2 wave is not always a standard blip wave, sometimes, it may be a flat-headed wave (e.g. FIG. 5D), or saddle-shape wave (e.g. FIG. 5E). In the case of FIG. 5D and FIG. 5E, the latency of N2 wave is the time corresponding to the mid-point of the flat or saddle-shaped wave crest. Typically, a negative wave between 30 ms and 90 ms is regarded as the N1 wave, however, occasionally there is a N1' wave shorter than 30 ms (e.g. FIG. 4F) which is disregarded, and the next wave is considered to be the N1 wave.

According to one particular embodiment of the pulsed flash of light applied to the eyes of a subject, and without limitation, the pulse frequency is 1 Hz and the pulse-width is 100 ms. The typical frequency of the pulsed flash of light is 1 Hz; however, other values may be used, such as 0.25 Hz, 0.5 Hz, or 0.75 Hz. The pulse-width of pulsed flash of light is typically 100 ms; however other values, normally in the range of 100 ms to 400 ms, may be used. The pulse frequency and pulse-width of the pulsed flash of light are chosen based on the age and clinical diagnosis of a subject. For the old or visual path injured patient, low flash frequency and wider pulse-width are used, such as 0.5 Hz and 200 ms pulse-width.

The FVEP signal measured by the electrodes is very weak and always noised by EEG signals; as such, the measured signal $x(n)$ includes the FVEP signal $s(n)$ and the EEG signal $u(n)$. According to one particular embodiment of the signal processing steps for extracting FVEP signal, shown in FIG. 6. With these signal processing steps, the EEG signal can be removed from the observed signal $x(n)$ in order to get the de-noised FVEP signal $s(n)$, which is useful for identifying N2 wave position.

Figure 6:
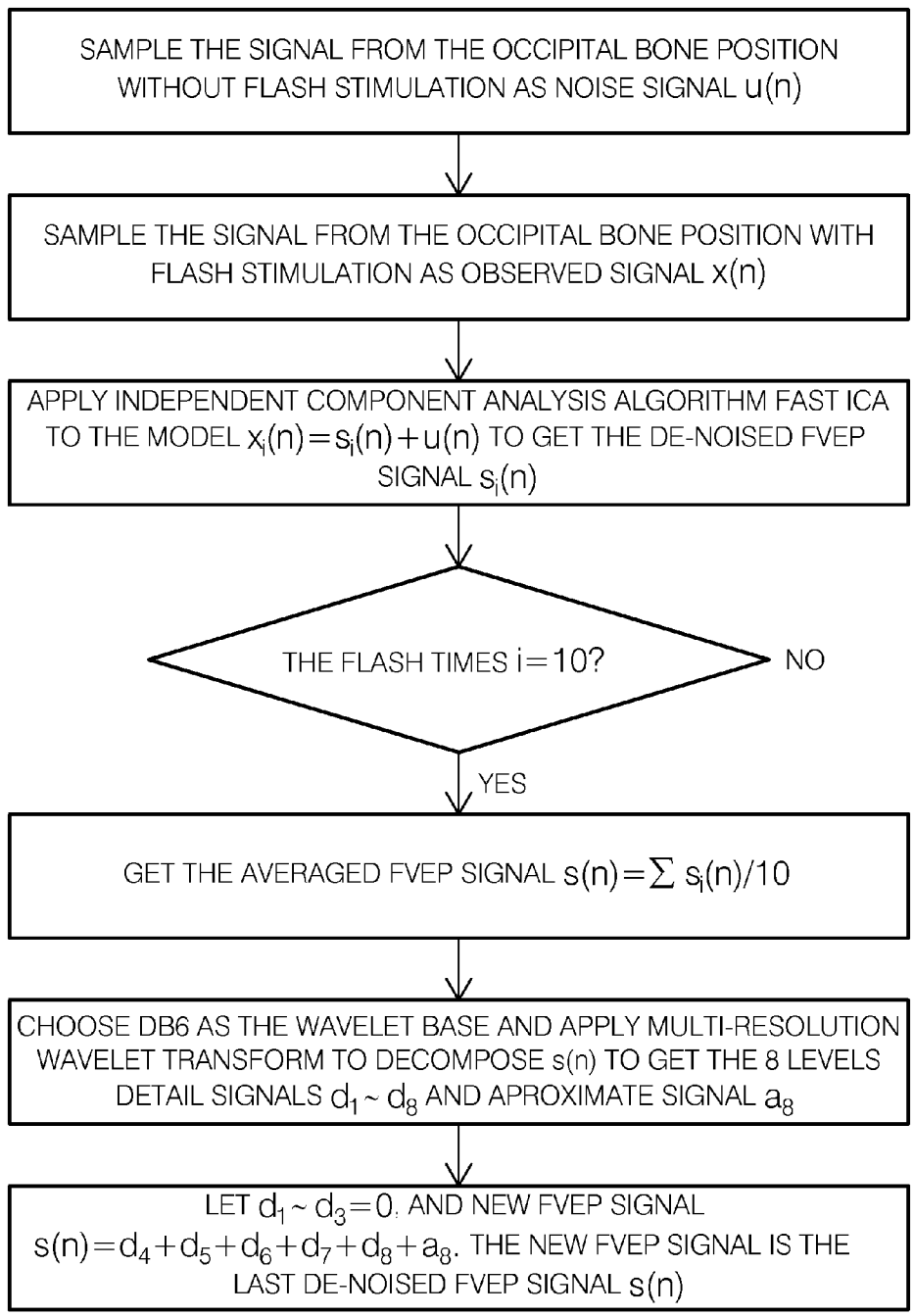
FIG. 6 illustrates a block diagram representing one embodiment of the signal processing performed on an FVEP signal detected by electrodes in the occipital lobes of a subject.

According to one particular embodiment of the steps for identifying the N2 wave position: the FVEP signal is extracted according to the steps shown in FIG. 6, then the decision logic is applied to the FVEP signal to determine the horizontal ordinate of the N2 wave, and finally the N2 wave position is marked graphically. These steps can be performed automatically or semi-automatically with correction by a trained professional.

According to one embodiment a system for determining intracranial pressure (ICP), comprises: (a) a transcranial Doppler (TCD) instrumentation apparatus configured to determine the middle cerebral artery (MCA) velocity of the subject and estimating changes in the ICP continuously based on a functional mapping that relates arterial blood pressure (ABP) and cerebral blood flow velocity (CBFV) to ICP, resulting in an estimated ICP trend; (b) flash visual evoked potential instrumentation apparatus configured for generating a flash visual evoked potential (FVEP) on the subject, processing a detected FVEP signal and obtaining an estimated ICP; and (c) a computing apparatus configured for combining the estimated ICP trend from TCD CBFV and ABP with the estimated ICP obtained by signal processing of the detected FVEP signal to periodically correct the trend and outputting a non-invasive measure of ICP.

According to a particular disclosed embodiment, and without limitation, a system for monitoring the intracranial pressure of a subject by application of flash visual evoked potential, comprises: (a) a signal processing device adapted to trigger operation of a flash stimulation device, receive and process electrical signals from electrodes, and output enhanced electrical signals to a computing device, the signal processing device includes a power supply and 1 the logic includes at least one high gain amplifier and an analog-to-digital converter; (b) a flash stimulation device electrically connected to the signal processing device, the flash stimulation device includes two embedded light diode arrays suitable for placement near each eye of a subject; (c) a plurality of disc-like electrodes or Ag/AgCl needles electrically connected to the signal processing device; and (d) a computing device configured to receive the enhanced electrical signals from the signal processing device via a communication link, the computing device includes data storage, a visual display, and software adapted to process, store, and display a representation of the enhanced electrical signals; whereby the intracranial pressure of the subject can be determined by analysis of said enhanced electrical signals.

Figure 2:
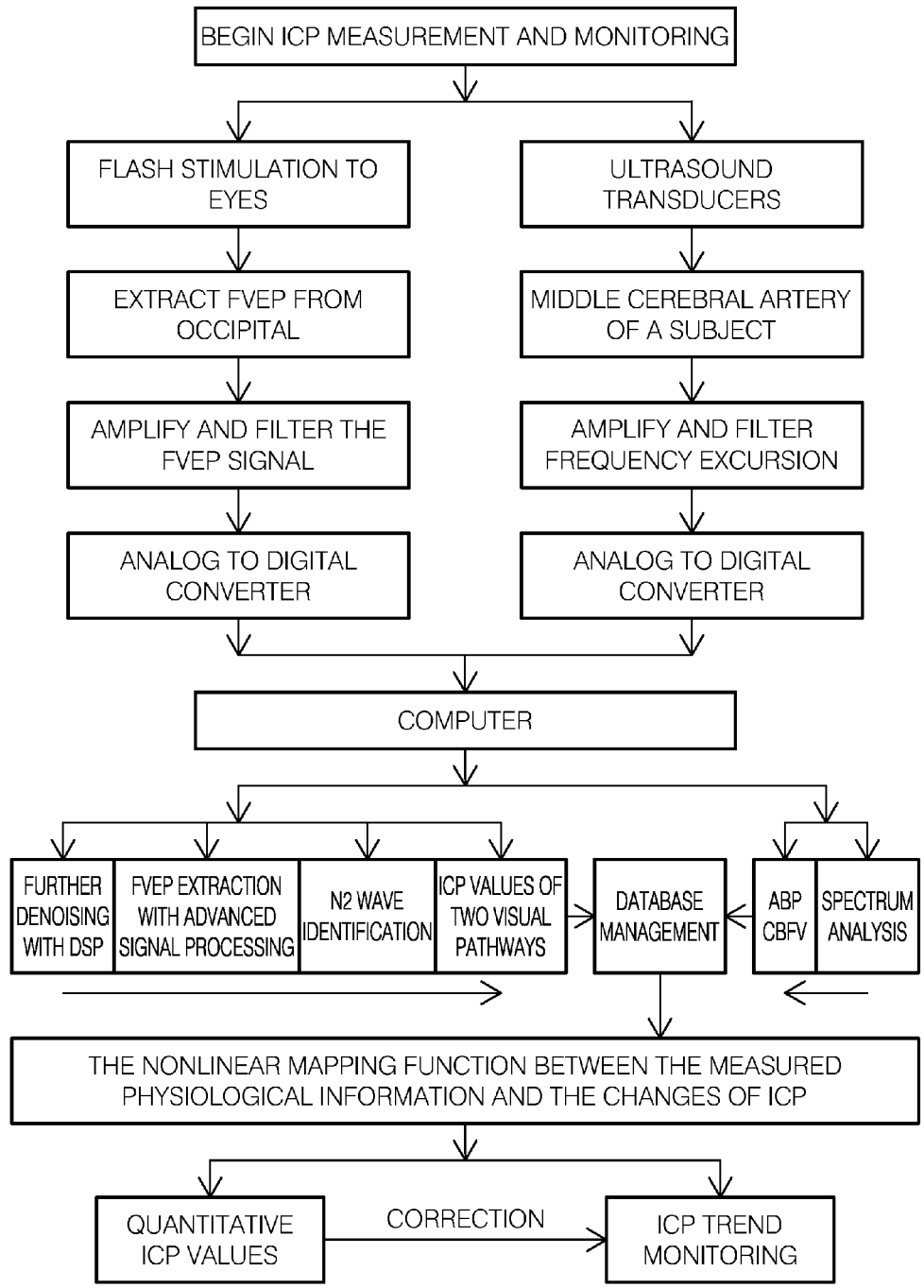
FIG. 2 shows a block diagram according to one embodiment of the system and method.

According to one particular embodiment of a system for non-invasive (or minimally invasive) monitoring of ICP of a subject, system components comprise a flash stimulation device, electrodes, a signal processing device, a personal computer (PC), and an optional printer for printing the detected and analyzed results. The flash stimulation device is an eye-patch with two embedded light diode arrays for stimulation of each eye of a subject. The electrodes are disc-like electrodes electrically connected to the input of the signal processing device. In one particular embodiment, and without limitation, the signal processing device includes two high gain amplifiers, a data acquisition card (e.g., NI DAQ M), and power supply. The output of the amplifiers is connected to analog inputs of the data acquisition card, which performs analog to digital conversion of the incoming FVEP signals, which are then processed in a computer system. Upon commencement of applied FVEP, the flash stimulation device emits a standard optical excited signal (pulsed flash of light) to each eye, which are transformed into electrical signals by the retinas. The electrical signals propagate through the visual pathways to the occipital lobes and are picked up by the electrodes placed on the scalp over the occipital lobes. A reference electrode placed on the hair line of the forehead of said subject, and a ground electrode placed on the glabellum of said subject. The weak FVEP signals are amplified and converted to digital signals by the signal processing device to generate enhanced FVEP signals for processing by PC software. The software has a signal processing module for FVEP waveform extraction, an automatic diagnosis module to determine the latency of the N2 wave, a management module for patient information, and a graphical user interface for display of FVEP waveforms and software controls, shown in FIG. 2.

While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the method and system have been described with reference to various embodiments, it is understood that the words which have been used herein are words of description and illustration, rather than words of limitation. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A method for determining intracranial pressure (ICP) of a subject, comprising:
   (a) applying transcranial Doppler (TCD) to determine the middle cerebral artery (MCA) velocity of said subject and estimating changes in said ICP continuously based on a functional mapping that relates arterial blood pressure (ABP) and cerebral blood flow velocity (CBFV) to ICP, resulting in an estimated ICP trend;
   (b) generating a flash visual evoked potential (FVEP) on said subject, processing a detected FVEP signal, and obtaining an estimated ICP; and
   (c) combining said estimated ICP trend from TCD CBFV and ABP with said estimated ICP obtained by signal processing of said detected FVEP signal to periodically correct said trend and obtain a non-invasive measure of ICP.

2. The method for determining ICP of claim 1, wherein said obtaining an estimated ICP comprises:
   (a) applying a flash stimulation to the eyes of said subject resulting in a generated FVEP signal in the visual pathway of said subject;
   (b) detecting said generated FVEP signal by electrodes placed on the occipital area;
   (c) performing signal processing to amplify, filter, detect features, and measure a latency of a feature on the FVEP signal correlated with ICP; and
   (d) estimating ICP based on a functional mapping that relates said latency on the FVEP signal and ICP.

3. The method for determining ICP of claim 2, wherein said latency of a feature on the FVEP signal is obtained by measuring a latency change on said FVEP signal second negative wave (N2) wave.

4. The method for determining ICP claim 3, wherein said performing signal processing includes amplifying; filtering; and denoising said FVEP signal using independent component analysis (ICA) based on Fast ICA, synchronous averaging, and wavelet decomposition.

5. The method for determining ICP of claim 4, wherein said signal processing further includes identifying said N2 wave and deriving ICP values corresponding to the two visual pathways of said subject.

6. The method for determining ICP of claim 5, wherein identifying said N2 wave is performed automatically using digital signal processing (DSP) or semi-automatically depending on the condition of the FVEP signal.

7. The method for determining ICP of claim 6, wherein generating FVEP on said subject comprises:
   a) applying a plurality of disc-like electrodes or Ag/AgCl needle electrodes to the occipital lobes of said subject, said electrodes being electrically connected to a signal processing device;
   b) applying a pulsed flash of light to both eyes of said subject using a flash stimulation device, said pulsed flash having a pre-determined pulse frequency;
   c) capturing the resulting flash visual evoked potential signals generated in the left and right visual pathways to the occipital lobes of said subject by said signal processing device via said electrodes;
   d) performing signal processing on said flash visual evoked potential signals using said signal processing device, said signal processing including at least one high gain amplifier and an analog-to-digital converter, digital signal processing, and an output for enhanced flash visual evoked potential signals to a computing device;
   e) determining the latency value of the N2 wave of the flash visual evoked potential; and
   f) applying a predetermined linear relationship between latency of the second negative wave and invasive intracranial pressure to derive the intracranial pressure of said subject.

8. The method for determining ICP of claim 7, wherein said electrodes are solely disc-like electrodes, whereby intracranial pressure of said subject can be determined entirely non-invasively.

9. The method for determining ICP of claim 8, wherein said pre-determined frequency of said pulsed flash is adjustable.

10. The method for determining ICP of claim 9, wherein said plurality of disc-like electrodes or Ag/AgCl needle electrodes consists of four electrodes, two of said four electrodes are sampling electrodes placed on the occipital lobes of said subject, one of said four electrodes is a reference electrode placed on the hair line of the forehead of said subject, and one of said four electrodes is a ground electrode placed on the glabellum of said subject.

11. The method for determining ICP of claim 10, wherein displaying a representation of said enhanced flash visual evoked potential signals on said computing device further includes an option of displaying one of a group consisting of a representation of an enhanced flash visual evoked potential signal for said left visual pathway to the occipital lobes of said subject, a representation of an enhanced flash visual evoked potential signal for said right visual pathway to the occipital lobes of said subject, a representation of superimposed enhanced flash visual evoked potential signals for said left and right visual pathways to the occipital lobes of said subject, and a representation of any stored enhanced flash visual evoked potential signal or combination of enhanced flash visual evoked potential signals.

12. The method for determining ICP of claim 11, wherein determination of said latency value is based on a plurality of predetermined decision rules.

13. A system for determining intracranial pressure (ICP), comprising:
   (a) a transcranial Doppler (TCD) instrumentation apparatus configured to determine the middle cerebral artery (MCA) velocity of said subject and estimating changes in said ICP continuously based on a functional mapping that relates arterial blood pressure (ABP) and cerebral blood flow velocity (CBFV) to ICP, resulting in an estimated ICP trend;
   (b) a flash visual evoked potential instrumentation apparatus configured for generating a flash visual evoked potential (FVEP) on said subject and processing a detected FVEP signal and obtaining an estimated ICP; and
   (c) a computing apparatus configured for combining said estimated ICP trend from TCD CBFV and ABP with said estimated ICP obtained by signal processing of said detected FVEP signal to periodically correct said trend and outputting a non-invasive measure of ICP.

* * * * *